US008496612B2

(12) United States Patent (10) Patent No.: US 8,496,612 B2
Cude (45) Date of Patent: *Jul. 30, 2013

(54) ADAPTER FOR POWER INJECTIONS

(75) Inventor: J. Michael Cude, College Grove, TN (US)

(73) Assignee: Coeur, Inc., Lebanon, TN (US)

( * ) Notice: Subject to any disclaimer, the term of this patent is extended or adjusted under 35 U.S.C. 154(b) by 376 days.

This patent is subject to a terminal disclaimer.

(21) Appl. No.: 12/702,783

(22) Filed: Feb. 9, 2010

(65) Prior Publication Data

US 2010/0137714 A1 Jun. 3, 2010

Related U.S. Application Data

(63) Continuation of application No. 11/865,787, filed on Oct. 2, 2007, now Pat. No. 7,658,722, and a continuation of application No. PCT/US2007/080301, filed on Oct. 3, 2007.

(60) Provisional application No. 60/955,280, filed on Aug. 10, 2007.

(51) Int. Cl.
*A61M 31/00* (2006.01)

(52) U.S. Cl.
USPC .......................................................... 604/65

(58) Field of Classification Search
USPC ......................................... 604/65–69, 890.1
See application file for complete search history.

(56) References Cited

U.S. PATENT DOCUMENTS

| 4,636,198 | A | 1/1987 | Stade |
| 4,976,696 | A | 12/1990 | Sanderson |
| 5,279,569 | A | 1/1994 | Neer et al. |
| 5,383,858 | A | 1/1995 | Reilly et al. |
| 5,429,602 | A | 7/1995 | Hauser |
| 5,520,653 | A | 5/1996 | Reilly |
| 5,814,015 | A | 9/1998 | Gargano et al. |
| 5,947,929 | A | 9/1999 | Trull |
| 5,997,502 | A | 12/1999 | Reilly et al. |
| 6,080,136 | A | 6/2000 | Trull et al. |
| 6,090,064 | A | 7/2000 | Reilly et al. |
| 6,312,410 | B1 | 11/2001 | Yamamoto |
| 6,402,717 | B1 | 6/2002 | Reilly et al. |
| 6,402,718 | B1 | 6/2002 | Reilly et al. |
| 6,475,192 | B1 | 11/2002 | Reilly et al. |
| 6,685,678 | B2 | 2/2004 | Evans et al. |
| 6,733,478 | B2 | 5/2004 | Reilly et al. |
| 6,808,513 | B2 | 10/2004 | Reilly et al. |
| 7,018,363 | B2 | 3/2006 | Cowan et al. |
| 7,029,459 | B2 | 4/2006 | Reilly |
| 7,081,105 | B2 | 7/2006 | Reilly |
| 2003/0065287 | A1 | 4/2003 | Spohn et al. |
| 2004/0096313 | A1 | 5/2004 | Harvey et al. |
| 2004/0116861 | A1 | 6/2004 | Trocki et al. |

*Primary Examiner* — Manuel Mendez
*Assistant Examiner* — Rebecca E Eisenberg
(74) *Attorney, Agent, or Firm* — Hahn, Loeser & Parks, LLP

(57) ABSTRACT

A syringe adapter includes an adapter body having a first connecting portion that may be received into a power injector unit used to deliver contrast media. The adapter also includes a second connecting portion configured to receive the rearward end of an associated syringe. The adapter includes means for encoding information about the associated syringe that may be communicated to the power injector unit through one or more sensors. The means for encoding information may include a mechanism that moves linearly laterally back and forth to activate an actuator used to convey the encoded information. In particular, the action of installing the adapter may be decoupled from the action of encoding information.

10 Claims, 7 Drawing Sheets

ADAPTER FOR POWER INJECTIONS

CROSS-REFERENCE TO RELATED APPLICATIONS

This application is a continuation application of International Application No. PCT/US07/080301, filed Oct. 3, 2007, and a continuation of U.S. patent application Ser. No. 11/865,787, filed Oct. 2, 2007, which both claim priority from and the benefit of U.S. Provisional Application No. 60/955,280, filed Aug. 10, 2007. The disclosures of all these applications are incorporated in their entireties herein by reference.

TECHNICAL FIELD

The present invention pertains to syringes and syringe adapters used in conjunction with power injectors, and more particularly, to syringe adapters that convey encoded information to a power injector about a corresponding syringe.

BACKGROUND OF THE INVENTION

Injectors are devices that expel fluid, such as contrast fluid, into a circulatory system, which is used to enhance medical imaging like for example x-ray or magnetic imaging. The contrast fluid or contrast media is injected from a syringe, through a tube, and into an animal subject or human patient. Injectors are well known for use with a powered injector unit that is frequently fixed to a stand or support. Injectors typically include a plunger drive that couples to the plunger of the syringe and moves the plunger forward to expel fluid into the tube thereby injecting the contrast media in the subject.

Powered injectors or motorized injectors often include circuitry that controls the plunger drive unit for setting the rate of injection and/or the amount of fluid injected. Typically, the control circuitry includes switches which allow a user to manually actuate the drive unit to move the plunger within the syringe. The injector may cycle the plunger through the syringe one or more times to fill the syringe with fluid and expel any air bubbles trapped inside. Other syringes come pre-filled, which reduces the number of plunger drive movements needed to prepare the injector for a new injection. After the procedure has ended, the syringe plunger, typically positioned at the forward end of the syringe barrel, is retracted so that the syringe may be removed from the injector. In some injectors, the syringe can only be removed or replaced while the plunger drive is fully retracted.

Excess contrast media remaining in a syringe after an injection must be discarded as is well known in medical procedures to prevent cross contamination and/or infection. However, contrast media can be expensive. For this reason, when preparing for an injection, an empty syringe is filled with only as much media as will be needed for the next procedure. Similarly, pre-filled syringes are sold in a number of sizes, for example ranging from 60 to 200 milliliters, allowing the operator preparing for an injection to select a syringe containing only as much media as is needed for that procedure. Accordingly, the syringes may have one or more characteristic properties or parameters that if communicated to the power injector would assist the operator in the procedure and provide safeguards for ensuring proper use of the contrast media. Examples of such parameters may include syringe diameter or length, syringe material, contrast fluid composition and concentration of the contrast media. These parameters may affect certain procedures like the delivery rate or pressure.

Some syringes include information encoded into the surface of the syringe. When the syringe is inserted and rotated, the power injector reads and processes the information accordingly. In this situation, customized syringes must be used with a specific power injector. What is needed is an adapter that encodes and provides information to the powered injector unit for generic types of contrast media syringes.

BRIEF SUMMARY

In one embodiment of the subject invention an adapter for an associated injector unit used to inject fluid includes an adapter body having a first connecting portion for installing the adapter onto the associated power injector unit, wherein the adapter body includes a second connecting portion for receiving an associated syringe, a mechanism for encoding information about the associated syringe received at least partially within the adapter body, and wherein activation of the mechanism for encoding information is decoupled from connecting the adapter body to the associated power injector unit.

In one aspect of the embodiments of the subject invention associated information about the syringe is operable to be communicated to the associated power injector unit after the adapter has been installed into the associated power injector unit.

In another aspect of the embodiments of the subject invention, the mechanism for encoding information comprises a lever received at least partially within the adapter body.

In still aspect of the embodiments of the subject invention, the associated power injector unit includes one or more associated sensor inputs, and wherein the adapter also includes at least a first pin slidably received at least partially within the adapter body.

In even another aspect of the embodiments of the subject invention, the lever is a cam member for actuating the at least a first pin and includes a cam slot, and where the at least a first pin includes a first end operatively communicated to the cam slot.

In another aspect of the embodiments of the subject invention, the at least a first pin is L-shaped.

In yet another aspect of the embodiments of the subject invention, the adapter includes an indicator for indicating the operating status of the mechanism for encoding information.

Another embodiments of the subject invention includes a system for injecting contrast media in a subject that includes a power injector unit having a plunger driver movably received at least partially within the power injector unit, wherein the power injector unit includes one or more sensors for reading information about an associated syringe, an adapter body having a first connecting portion for selectively connecting the adapter to the power injector unit, wherein the adapter body includes a second connecting portion for receiving the associated syringe, the adapter including a mechanism for communicating information to the one or more sensors, the mechanism for communicating information being operatively received at least partially within the adapter body, and where activation of the mechanism for communicating information is decoupled from connecting the adapter body to the power injector unit.

In another embodiment of the subject invention a method for communicating information about an associated syringe to an associated power injector unit, includes the steps of providing an adapter body having a first and second connecting portions, providing a mechanism for encoding information about the associated syringe, installing the adapter body onto the associated power injector unit, and subsequently activating the mechanism for encoding information.

In one aspect of the embodiments of the subject invention, activating the mechanism for encoding information is decoupled from installing the adapter body.

In another aspect of the embodiments of the subject invention, the mechanism for encoding information is linearly actuated with respect to the adapter body.

DETAILED DESCRIPTION OF THE INVENTION

Figure 1:
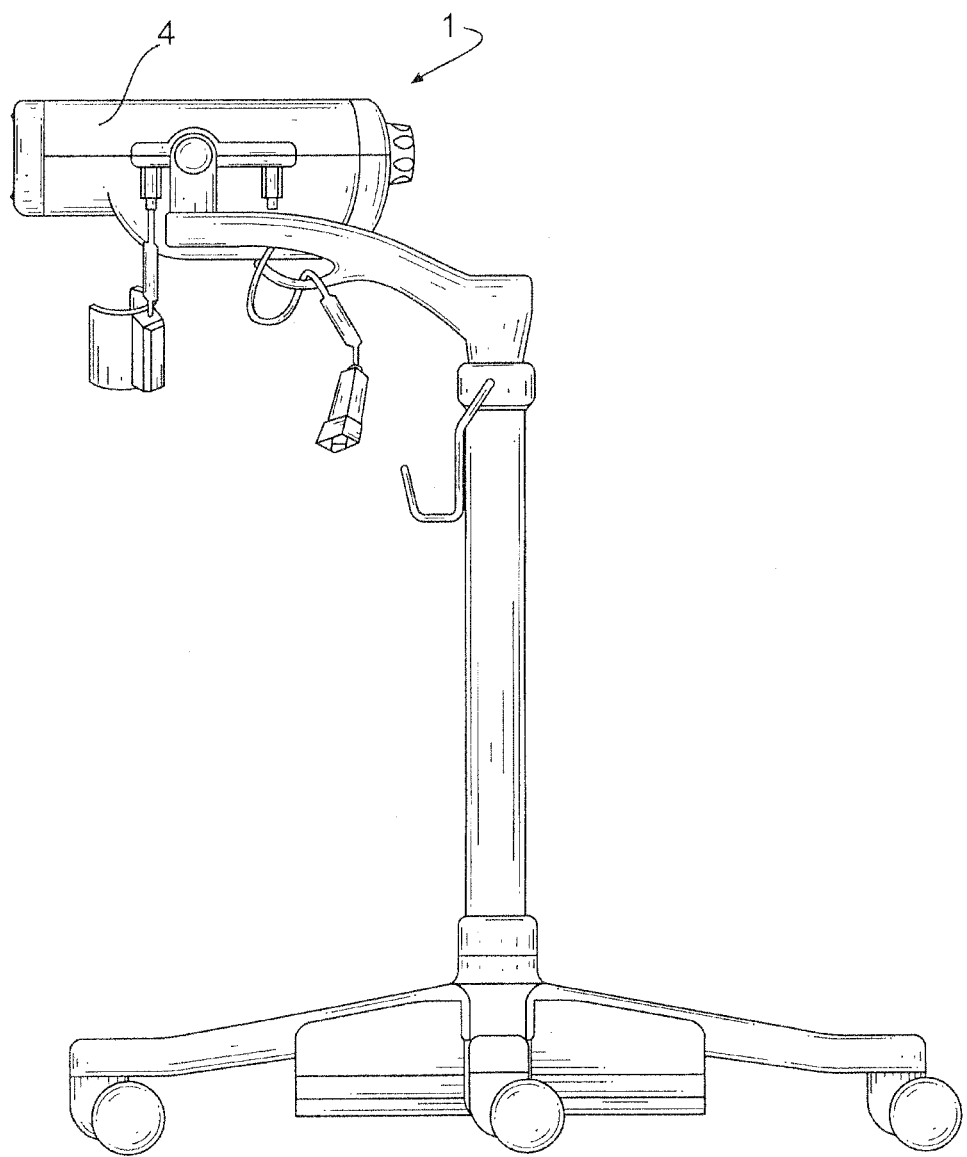
FIG. 1 is a perspective view of a power injector unit mounted to a support stand according to the embodiments of the subject invention.
Figure 1A:
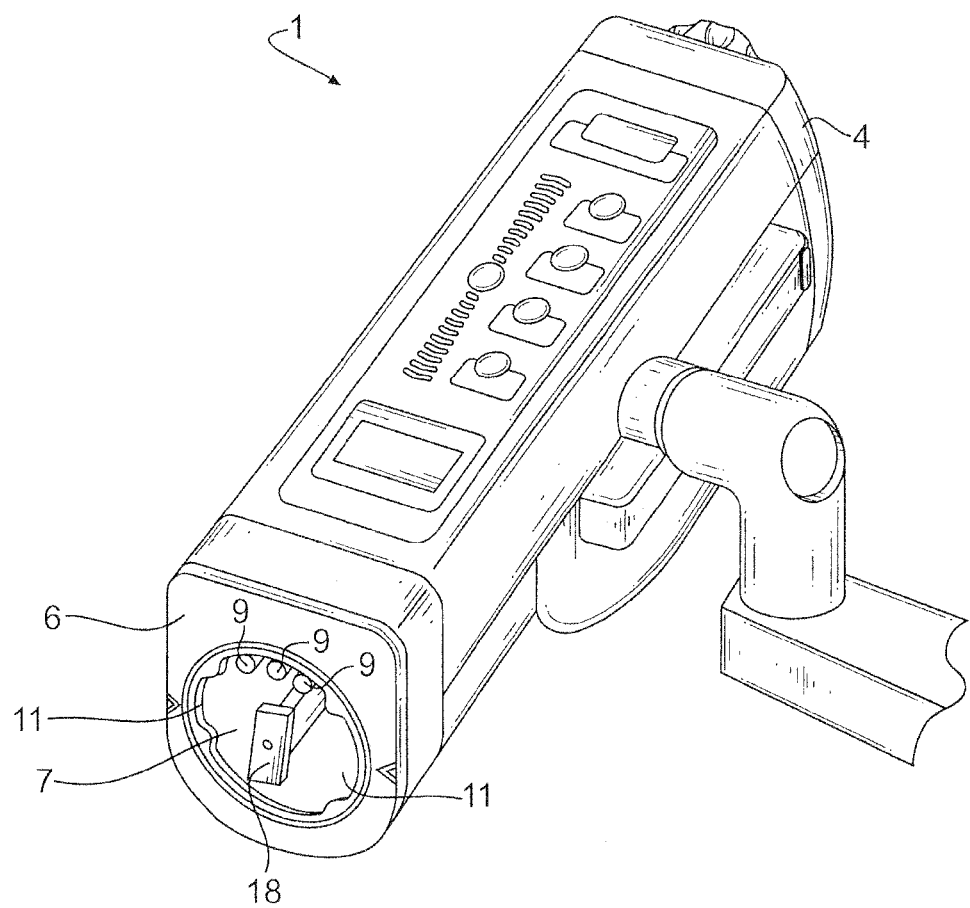
FIG. 1a is a perspective view of a power injector unit according to the embodiments of the subject invention.
Figure 2:
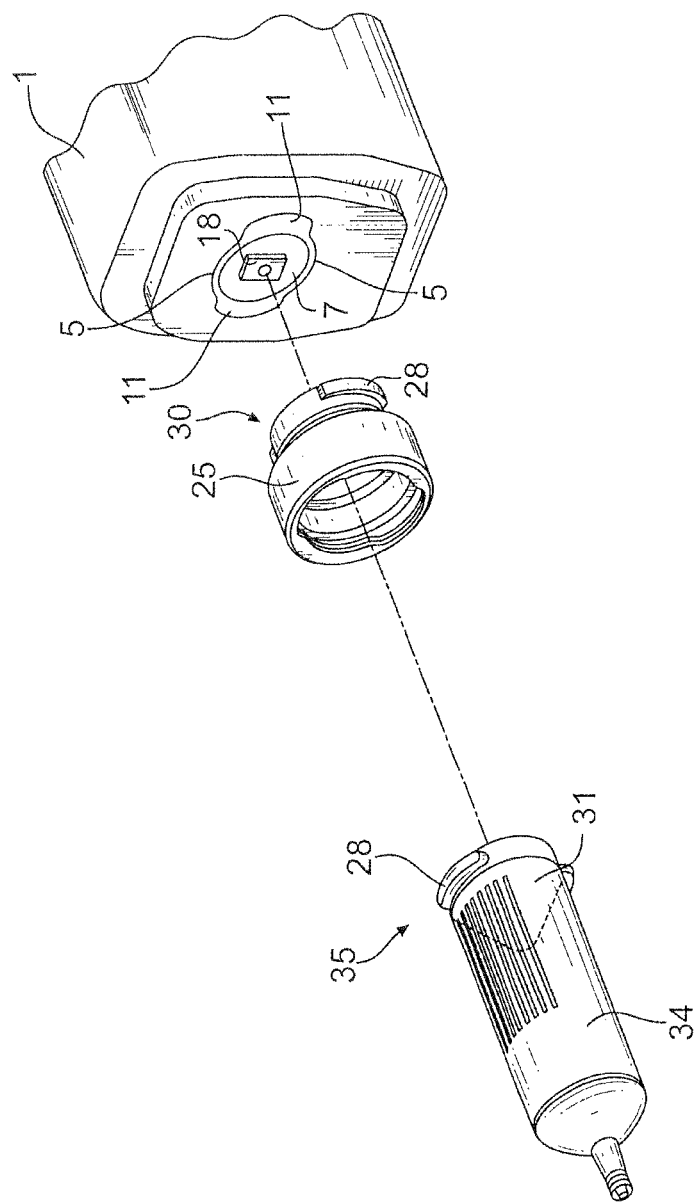
FIG. 2 is an exploded view of a syringe, syringe adapter and power injector unit according to the embodiments of the subject invention.

Referring now to the drawings wherein the showings are for purposes of illustrating embodiments of the invention only and not for purposes of limiting the same, FIGS. 1, 1a and 2 show a power injector unit depicted generally at 1. The power injector unit 1 includes a housing 4 having a front face 6 that may receive the rearward end 30 of an adapter 25 or the rearward end of a syringe 34. The front face 6 may include an opening 7 exposing a plunger driver 18 mounted within the housing 4. The plunger driver 18 functions to actuate the plunger 31, which controls the injection of fluid contained in the syringe 34. The syringe 34 may be used to inject contrast media or other fluid into a system, which may for example be the vascular system of an animal subject or human patient. However, it is noted that the scope of coverage of the embodiments of the subject invention may extend to any application utilizing power injector units. Slots 11 may be formed in the opening 7 of the front face 6 for receiving respective flanges 28 of the adapter 25. As such, the opening 7 may comprise a mounting block for receiving the adapter 25. The power injector unit 1 may further include a control console, not shown, incorporating a logic processor and other support circuitry for controlling and operating the power injector unit. Alternatively, the logic processor and/or support circuitry may be located within the housing 4 of the power injector unit 1. In any case, the logic processor may receive feedback data from one or more sensors 9 mounted proximate to the opening 7 for detecting information encoded within the adapter 25. The sensors 9 may be operable to detect not only the presence of an adapter 25 installed into the power injector unit 1, but also other characteristic properties of the associated syringe 34 as will be discussed further in a subsequent paragraph.

The adapter 25 may be installed into the power injector unit 1 by inserting the rearward end 30 of the adapter 25 into the opening 7 through the slots 11. While the figures illustrate two slots 11 and two flanges 28, any configuration of the opening 7 and corresponding flanges 28 may be chosen with sound engineering judgment. Mounting rims 5 may extend at least partially around the circumference of the opening 7 in between the slots 11, and may include grooves respectively fashioned behind the mounting rims 5. It should be readily seen that subsequently rotating the adapter 25 will engage the flanges 28 with respect to the underside of the mounting rims 5 thereby securing the adapter 25 in position. The adapter 25 may include a system or mechanism for encoding information. The mechanism may interface with the sensors 9 and communicate data about the corresponding syringe 34. After the adapter 25 has been secured to the power injector unit 1, the mechanism for encoding information may be then activated thereby engaging the sensors 9 and communicating information about the syringe 34 to the power injector unit 1. It is noted here that securing the adapter 25 to the power injector unit 1 may be a distinctly separate action from encoding information or communicating information about the syringe 34 to the power injector unit 1. In other words, the action of securing the adapter 25 to the power injector unit 1 is decoupled or independent from the action of encoding information about the syringe 34, which will be discussed in detail below. Set up may further include the insertion of the syringe 34 into the adapter 25, where after the plunger driver 18 may be activated and connected to the syringe plunger 31 in a manner well-known in the art. It is noteworthy that not only is the action of securing the adapter 25 decoupled from the action of encoding information, but the action of securing or installing the syringe 34 to the adapter 25 is also decoupled from the action of encoding information about the syringe 34. The step of engaging the sensors 9, or communicating information to the sensors 9, is an independent step in the process of using of the power injector unit 1.

Figure 3:
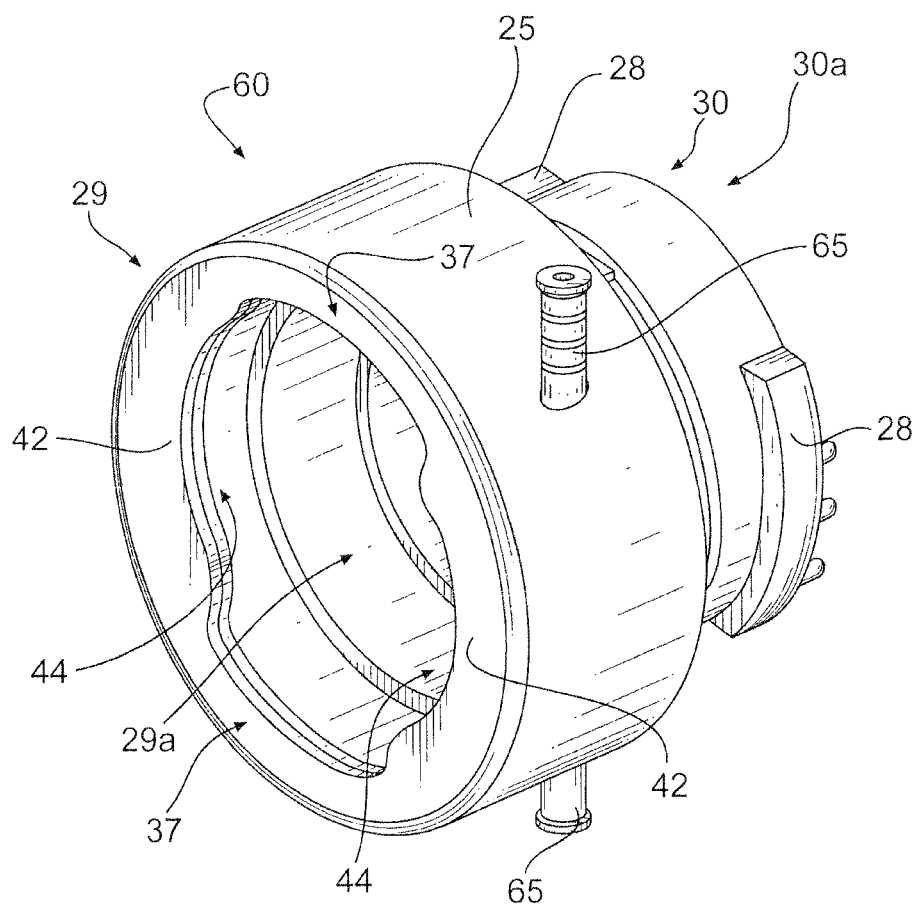
FIG. 3 is a perspective view of the syringe adapter according to the embodiments of the subject invention.
Figure 4:
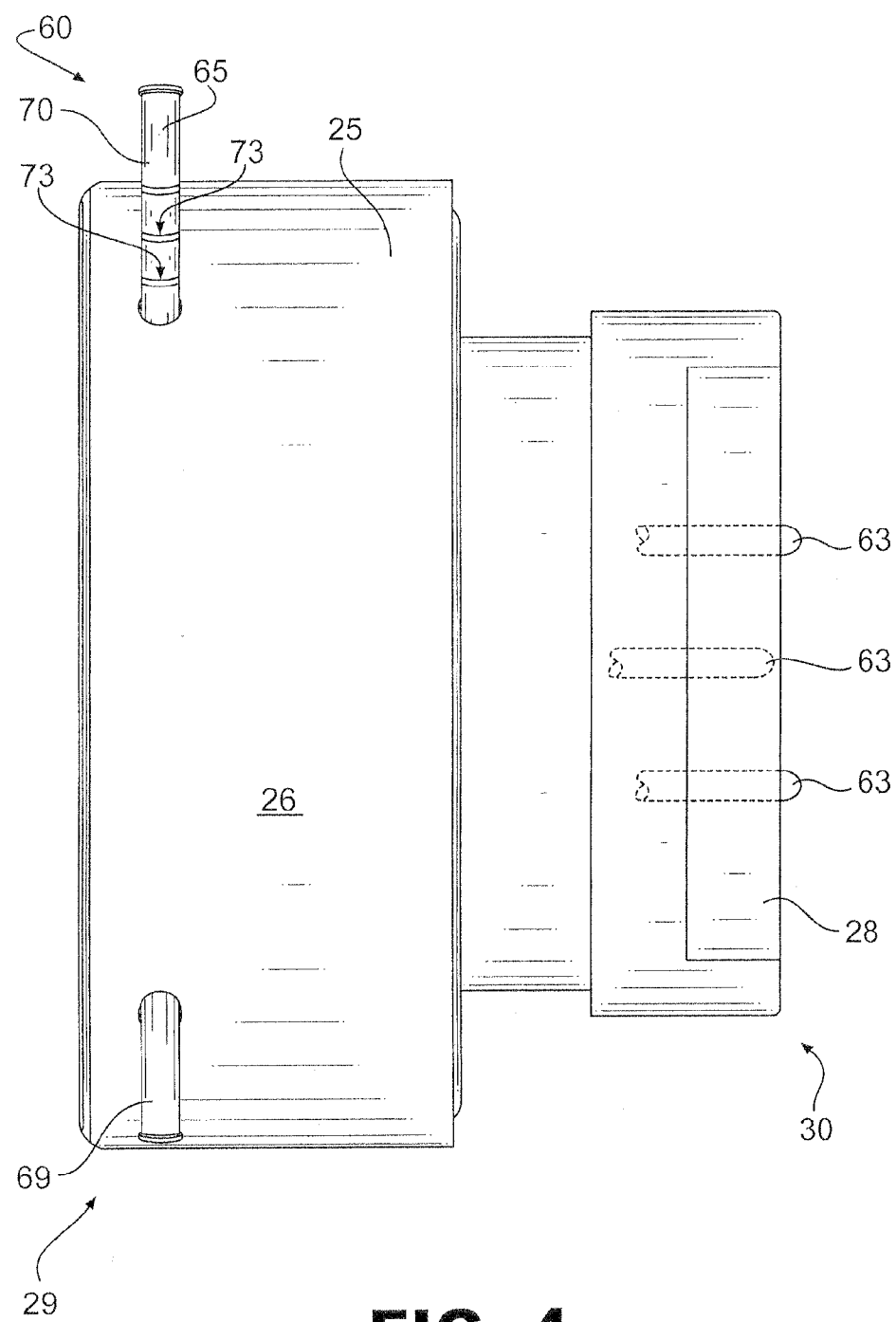
FIG. 4 is a perspective side view of the syringe adapter according to the embodiments of the subject invention.

With reference now to FIGS. 3 and 4, the adapter 25 is described herein as having first and second ends 29, 30. The first end 29 of the adapter 25 may include a first opening 29a, which may be configured to receive the rearward end 35 of the syringe 34. It is noted that syringes mounted in this manner are referred to as being front-loaded. The second end 30 of the adapter 25 may include first and second flanges 28, as previously mentioned. The flanges 28 may be used to mount the adapter 25 in place with respect to the opening 7 of the power injector unit 1. Accordingly, the second end 30 of the adapter 25 may include a second opening 30a through which the plunger driver 18 may extend to engage the plunger 31 of the syringe 34. It follows that the adapter 25 therefore includes an internal cavity that extends from the first opening 29a to the second opening 30a. In this manner, the plunger driver 18 may be driven forward through and retracted from the adapter 25 when actuating the plunger 31. It is noted that while the adapter 25 is illustrated in the figures as being generally cylindrical, any geometric configuration of the adapter 25 may be chosen as is appropriate for use with the embodiments of the subject invention.

The first opening 29a may include slots 37, similar to the slots 11 fashioned in the front face 6 of the power injector unit 1. The slots 37 may be fashioned at distal sides of the first opening 29a and may be used to receive flanges 28 extended from the rearward end 35 of the syringe 34. In one embodiment, the slots 37 may be substantially 180° apart. However, any quantity and configuration of slots 37 may be chosen without departing from the intended scope of coverage of the embodiments of the subject invention. Retaining ledges 42 may be fashioned circumferentially around the opening 29a in between the slots 37. The underside of the retaining ledges 42 may further contain grooves 44 that may be used to engage the flanges 28 of the syringe 34 for mounting the syringe 34 in place with respect to the adapter 25. A stop member, not shown, may be included to limit rotation and thus fix the position of the syringe 34. In this way, the syringe 34 may be mounted to the adapter 25 in substantially the same way that the adapter 25 is mounted into the power injector unit 1. It will be appreciated that the mounting configuration of the syringe 34, the adapter 25, and the opening 7 of the injection unit 1 is not to be construed as limiting. Rather other mounting configurations may be chosen without departing from the intended scope of coverage of the embodiments of the subject invention.

With continued reference to FIGS. 3 and 4, as mentioned above, the adapter 25 may include a system 60 for encoding information about the syringe 34. The system may be substantially mechanical in nature. However, electrical or electronic systems 60 as well as hybrid systems 60 may be incorporated without departing from the intended scope of coverage of the embodiments of the subject invention. In an exemplary manner, the system 60 includes an actuator or actuators for communicating with the sensors 9, which may comprise a series of pins 63. The one or more actuators may be received within the body 26 of the adapter 25 and positioned such that when the adapter 25 is mounted into the power injector unit 1, the one or more actuators are positioned adjacent to the sensors 9. By positioned adjacent to the sensors it is meant that the actuators may be positioned in any manner so as to selectively engage the sensors 9. In one embodiment, the actuators may include one or more pins 63 slidably received into the body 26 of the adapter 25 and may be individually activated to convey information about the syringe 34. In the default position, the pins 63 may be substantially retracted into the body 26 of the adapter 25. When actuated, the pins 63 may be extended to engage or communicate with the sensors 9. It is noted here that any type of sensor 9 may be utilized to detect the presence or absence of the pins 63. Examples of such sensors may include proximity sensors or pressure sensors. Still, any type of sensors 9 may be utilized without limiting the scope of the coverage of the embodiments of the subject invention. In this manner, the sensors 9 may detect the presence or absence of the pins 63 responsive to being actuated by an actuating member 65 to be described below.

It will be appreciated by persons of ordinary skill in the art that distinctive information about the syringe 34 may be communicated via the sequence in which the pins 63 are actuated. Additionally, distinctive information may be communicated by the presence or absence of a particular pin 63 within a given sequence. In one embodiment, three pins 63 are illustrated as being received within the body 26 of the adapter 25, along with three corresponding sensor inputs. It will be readily seen that the pins 63 may represent binary states, in this example three, resulting in a total of 8 distinctive combinations. The distinctive combinations may represent any type of information about the syringe 34. Such information may include, but is not limited to: syringe diameter, syringe length, syringe volume, syringe material, syringe contents, operating pressure, flow rates, manufacturing lot numbers, dates and the like. In fact, any information about the syringe 34 may be encoded into the system 60 for communicating information as is appropriate for use with the embodiments of the subject invention. In one embodiment, one of the pins 63 may be dedicated to communicating the presence or absence of the adapter 25 mounted within the power injector unit 1. The remaining pins 63 may be utilized to convey actual information about the syringe 34 itself. For example, detection of the presence of a first pin and detection of the absence of a second pin may represent a particular size of syringe, like 60 mL.

Additionally, detection of the absence of the first pin and detection of the presence of the second pin may represent a syringe having a 125 mL volume. It follows that detection of the presence of both the first and second pins may represent yet another volume, which may be 200 mL. In another embodiment, detection of the pins may represent the type of contrast media and/or its concentration. Still, it is to be construed that any number of pins 63 may be incorporated into the embodiments of the present invention for communicating any type of data about the syringe 34 and/or the adapter 25 as chosen with sound engineering judgment.

As mentioned above, detection of the pins 63 may be accomplished by physical contact of an end of a pin 63 with the corresponding sensor 9 or sensor input, which may be a switch. As such the pins 63 may be constructed of a generally rigid or semi rigid material, such as plastic or metal. Alternatively, detection of the pins may be accomplished by non-contact sensors 9, which may electromagnetically, for example, detect the presence or absence of a particular pin 63. In this case, the pins 63 may be constructed from a ferrous material. Still, the sensors 9 may be comprised of any type of sensing mechanism. Additionally, the pins 63 may be constructed of any material suitable for detection by the sensors 9.

Figure 5:
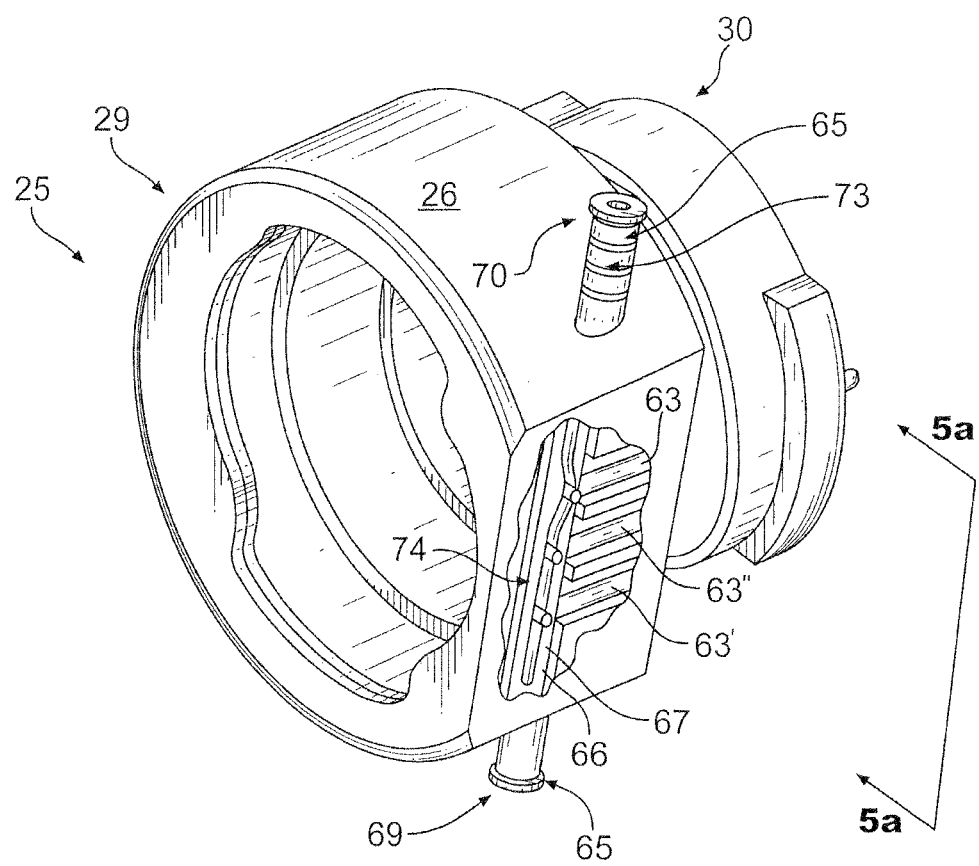
FIG. 5 is a partial perspective cutaway view of a syringe adapter that encodes information according to the embodiments of the subject invention.

With reference now to FIG. 5, the system 60 for encoding information may include an actuating member 65. In one embodiment, the actuating member 65 may include a lever 66 that engages each of the pins 63 in a sequential order. In this manner, a first pin 63' may be actuated and retracted prior to engaging the second pin 63", which correspondingly may be retracted prior to engaging the next pin. In a manner consistent with that described above, the presence or absence of a given pin 63 as detected by the sensors 9 may communicate to the power injector unit 1 specific information about the attached syringe 34. An alternate embodiment is contemplated wherein the lever 66 may actuate all of the pins 63 at substantially the same time. However, it is to be construed that any manner and/or sequence of actuating the pins 63 may be chosen as is appropriate for use with the embodiments of the present invention.

With continued reference to FIGS. 3 through 5, the lever 66 may be received at least partially within the body 26 of the adapter 25. The lever 66 may include a first and second ends 69, 70. In one embodiment, each of the first and second ends 69, 70 may extend outside the body 26 of the adapter 25. Accordingly, the first and second ends 69, 70 may be used by the operator to activate or initiate the process of communicating the encoded information to the power injector unit 1. Activation may be initiated by depressing one end of the lever 66 thereby translating the lever 66 about its longitudinal axis. It is noted here that activation of the lever 66 is generally linear in nature. That is to say that rotation is not needed to encode or communicate information to the power injector unit 1. The actuating member 65 may be manually activated by the user after or separate from installing the adapter 25 into the power injector unit 1. In this manner, installation of the adapter 25 is disassociated from activating the lever 66, which communicates information about the syringe 34 to the power injector unit 1. Each of the first and second ends 69, 70 may include an indicator 73 for indicating the status of communicating the encoded information to the power injector unit 1. The indicator 37 may comprise markings applied to the surface of the lever 66 at the first and second ends 69, 70 for depicting the status of the system 60 or the operating state of the lever 66. In one embodiment, the markings may include colored rings. For example, a first status or position of the lever 66 may be indicated by green rings signifying the readiness state of the system 60 for actuation and subsequent communication of the encoded information. A second status or position of the lever 66 may include red rings indicating that the system 60 or the position of the lever 66 is ready to be reset. Other embodiments may include alphanumeric or other characters for indicating the activation status of the lever 66. However, any means for indicating the activation status of the lever 66 may be chosen as is appropriate for use with the embodiments of the subject invention. In the current embodiment, communicating the encoded information takes place by activating the lever 66 in a first direction. As such, shifting the lever 66 in the opposite direction may function only to reset the power injector unit 1 for receiving the next batch of encoded information, which may come from the same or another adapter 25. It is noted here that an alternate embodiment is contemplated, wherein activating the lever 66 in either direction may activate the system 60 and thereby communicate the information encoded into the adapter 25.

Figure 5A:
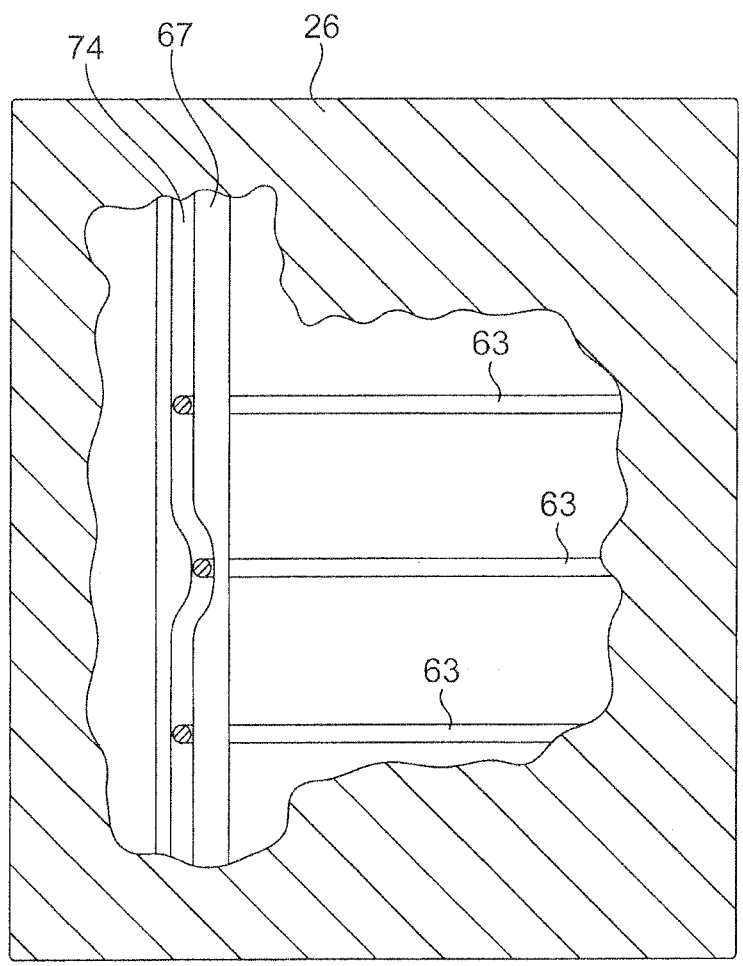
FIG. 5a is a cutaway view of the syringe adapter showing a cam member according to the embodiments of the subject invention.

With continued reference to FIG. 5 and now to FIG. 5a, in one embodiment, the lever 66 may be a cam member 67. The cam member 67 may include a cam slot 74 fashioned within the lever 66, which may receive the pins 63. Accordingly, the pins 63 may include cam followers for engaging the cam slot 74. In this manner, the pins 63 may be L-shaped and contiguously formed for translation by the cam member 67. As illustrated, the cam slot 74 may include a first generally linear portion followed by a second nonlinear portion, or cam portion. Continuing along the cam member 67, the cam portion flows back again into another generally linear portion. In this manner, activating the lever 66 forces each of the pins 63, in sequential order, downward as the pins 63 engage the cam portion thereby extending the respective pins 63 outside the adapter body 26 for detection by the sensors 9. To ensure alignment of the pins 63, apertures or slots may be fashioned in the body 26 of the adapter 25 and appropriately sized to receive and guide the pins 63. However, any means of aligning the pins 63 within the body 26 of the adapter 25 may be chosen with sound engineering judgment. It should be noted here that the configuration of the cam member 67 and the pins 63 are exemplary in nature. Persons of ordinary skill in the art should recognize that other means may also be employed to accomplish the desired effect.

With reference now to all of the Figures, operation of the adapter 25 will now be described. The adapter 25 may be oriented and inserted into the slots 11 of the power injector unit 1. The adapter 25 may then be rotated so that the flanges 28 engage the underside of the mounting rims 5 thereby securing the adapter in place. Additional fasteners may be utilized to secure the adapter 25 to the power injector unit 1. The operator may subsequently insert a syringe into the adapter 25. In a manner similar to that of the adapter 25, the syringe may likewise be rotated into engagement with the first opening of the adapter 25. The operator may then adjust the lever 66 in a first direction, which in a manner consistent with that described above may actuate the pins 63, received internal to the adapter 25, into detecting engagement with the sensors 9 of the power injector unit 1. After the procedure has been completed, the operator may slide the lever 66 in the opposite or second direction, thereby resetting the system 60 for the next procedure.

The invention has been described herein with reference to the preferred embodiment. Obviously, modifications and alterations will occur to others upon a reading and understanding of this specification. It is intended to include all such modifications and alternations in so far as they come within the scope of the appended claims or the equivalence thereof.

What is claimed is:

1. An adapter for a power injector unit used to inject fluid, comprising:
   an adapter body having a first connecting portion for installing the adapter onto the associated power injector unit, wherein the adapter body includes a second connecting portion for receiving an associated syringe;
   an encoding mechanism adapted to encode information about the associated syringe received at least partially within the adapter body; and,
   wherein the encoding mechanism adapted to encode information operates independently from the connection of the adapter body to the power injector unit.

2. The adapter as defined in claim 1, wherein the encoding mechanism adapted to encoding information is linearly actuated with respect to the adapter body.

3. The adapter as defined in claim 1, wherein associated information about an associated syringe is operable to be communicated to the power injector unit after the adapter has been installed into the power injector unit.

4. The adapter as defined in claim 1, wherein the encoding mechanism adapted to encode information comprises a lever received at least partially within the adapter body.

5. The adapter as defined in claim 4, wherein the power injector unit includes one or more associated sensor inputs, and further comprises:
   at least a first pin slidably received at least partially within the adapter body.

6. The adapter as defined in claim 5, wherein the lever is a cam member adapted to actuate the at least a first pin.

7. The adapter as defined in claim 5, wherein the lever includes a cam slot, and,
   wherein the at least a first pin includes a first end operatively communicated to the cam slot.

8. The adapter as defined in claim 7, wherein the at least a first pin is L-shaped.

9. The adapter as defined in claim 1, further comprising:
   an indicator for indicating an operating status of the encoding mechanism adapted to encode information.

10. The adapter as defined in claim 9, wherein the indicator comprises indicator markings applied to an outer surface of the encoding mechanism adapted to encode information.

* * * * *